US009808282B2

(12) United States Patent
Spenciner (10) Patent No.: US 9,808,282 B2
(45) Date of Patent: Nov. 7, 2017

(54) SURGICAL CANNULA SYSTEM AND METHOD OF USE

(71) Applicant: DePuy Synthes Products, Inc., Raynham, MA (US)

(72) Inventor: David B. Spenciner, North Attleboro, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 64 days.

(21) Appl. No.: 14/730,453

(22) Filed: Jun. 4, 2015

(65) Prior Publication Data

US 2016/0354113 A1 Dec. 8, 2016

(51) Int. Cl.
*A61B 1/32* (2006.01)
*A61B 17/34* (2006.01)

(52) U.S. Cl.
CPC .... *A61B 17/3421* (2013.01); *A61B 2017/349* (2013.01); *A61B 2017/3484* (2013.01); *A61B 2017/3492* (2013.01)

(58) Field of Classification Search
CPC ............ A61B 17/3423; A61B 17/3403; A61B 17/3405; A61B 17/3429; A61B 2017/34; A61B 2017/3488; A61B 2017/349; A61B 2017/3492
See application file for complete search history.

(56) References Cited

U.S. PATENT DOCUMENTS

| 3,397,699 A | * | 8/1968 | Kohl | A61M 25/04 29/451 |
|---|---|---|---|---|
| 4,418,693 A | | 12/1983 | LeVeen et al. | |
| 4,809,679 A | | 3/1989 | Shimonaka et al. | |
| 4,973,301 A | * | 11/1990 | Nissenkorn | A61F 2/94 604/8 |
| 5,122,122 A | * | 6/1992 | Allgood | A61B 17/34 604/105 |
| 5,203,773 A | * | 4/1993 | Green | A61B 17/34 604/104 |
| 5,217,441 A | * | 6/1993 | Shichman | A61B 17/3403 604/164.01 |
| 5,391,156 A | * | 2/1995 | Hildwein | A61B 17/29 411/503 |
| 5,540,658 A | * | 7/1996 | Evans | A61B 17/42 604/101.04 |
| 5,545,179 A | | 8/1996 | Williamson, IV | |

(Continued)

*Primary Examiner* — Eduardo C Robert
*Assistant Examiner* — Michelle C Eckman (57) ABSTRACT

Various methods and devices are provided for use of a cannula. For example, provided herein is a flexible cannula having an elongate body with an elongate shaft extending between a proximal hub and a distal dam. A lumen can extend through the cannula. The dam is in the form of a flexible annular member formed on a distal end of the shaft. The dam and the hub have diameters greater than a diameter of the shaft. A flexible, expandable sleeve is removably positioned on the distal end of the shaft of the cannula. The sleeve deformably encapsulates the dam such that the dam is folded against the shaft of the cannula. An obturator is also provided having an elongate shaft configured to be removably positioned within the lumen of the cannula. The shaft can be configured to fit within the lumen in a clearance fit.

20 Claims, 6 Drawing Sheets

(56) References Cited

U.S. PATENT DOCUMENTS

| | | | | |
|---|---|---|---|---|
| 5,569,159 | A * | 10/1996 | Anderson | A61B 1/00147 600/114 |
| 5,628,753 | A * | 5/1997 | Cracauer | A61B 17/3415 604/158 |
| 5,637,097 | A * | 6/1997 | Yoon | A61B 17/3417 604/104 |
| 5,685,857 | A * | 11/1997 | Negus | A61B 17/3423 604/164.11 |
| 5,707,362 | A * | 1/1998 | Yoon | A61B 17/3417 604/164.03 |
| 5,817,062 | A * | 10/1998 | Flom | A61B 17/3417 604/104 |
| 5,824,002 | A | 10/1998 | Gentelia et al. | |
| 5,836,913 | A * | 11/1998 | Orth | A61B 17/3417 604/107 |
| 5,888,196 | A * | 3/1999 | Bonutti | A61B 17/0218 600/153 |
| 5,941,898 | A * | 8/1999 | Moenning | A61B 17/3423 604/99.02 |
| 5,951,588 | A * | 9/1999 | Moenning | A61B 17/3423 604/104 |
| 6,171,282 | B1 | 1/2001 | Ragsdale | |
| 6,210,397 | B1 * | 4/2001 | Aboul-Hosn | A61B 17/3423 604/164.11 |
| 6,228,063 | B1 * | 5/2001 | Aboul-Hosn | A61B 17/3423 604/174 |
| 6,358,266 | B1 * | 3/2002 | Bonutti | A61B 17/3439 600/207 |
| 6,451,041 | B1 * | 9/2002 | Moenning | A61B 17/3417 604/164.04 |
| 6,620,129 | B2 * | 9/2003 | Stecker | A61M 1/0084 604/107 |
| 6,632,197 | B2 * | 10/2003 | Lyon | A61B 17/3421 604/106 |
| 6,743,207 | B2 * | 6/2004 | Elbert | A61B 17/3415 604/164.01 |
| 6,749,601 | B2 | 6/2004 | Chin | |
| 6,808,492 | B2 * | 10/2004 | Snyder | A61B 17/3421 600/114 |
| 6,918,888 | B2 * | 7/2005 | Gershowitz | A61M 25/10 604/107 |
| 6,929,663 | B2 * | 8/2005 | Rioux | A61M 25/04 600/29 |
| 7,347,866 | B2 * | 3/2008 | Daignault | A61M 25/04 604/104 |
| 7,377,897 | B1 * | 5/2008 | Kunkel | A61B 17/3421 600/184 |
| 7,470,247 | B2 * | 12/2008 | Aliski | A61F 2/04 604/8 |
| 7,641,664 | B2 * | 1/2010 | Pagano | A61B 17/025 606/92 |
| 7,691,089 | B2 * | 4/2010 | Gresham | A61B 17/3417 604/174 |
| 7,798,998 | B2 * | 9/2010 | Thompson | A61B 17/3421 604/164.04 |
| 7,806,870 | B2 * | 10/2010 | Mastri | A61B 17/3421 604/164.04 |
| 7,828,727 | B2 * | 11/2010 | Bhatnagar | A61B 17/02 600/201 |
| 8,038,652 | B2 | 10/2011 | Morrison et al. | |
| 8,043,319 | B2 | 10/2011 | Lyon et al. | |
| 8,137,267 | B2 | 3/2012 | Shelton, IV et al. | |
| 8,157,833 | B2 * | 4/2012 | Au | A61B 17/34 606/105 |
| 8,221,317 | B2 * | 7/2012 | Maynard | A61B 17/0218 600/204 |
| 8,262,568 | B2 * | 9/2012 | Albrecht | A61B 17/0293 600/206 |
| 8,357,088 | B2 * | 1/2013 | Shelton, IV | A61B 17/3423 600/215 |
| 8,388,660 | B1 * | 3/2013 | Abdou | A61B 17/8685 606/267 |
| 8,414,483 | B2 * | 4/2013 | Farrell | A61B 1/32 600/206 |
| 8,435,174 | B2 | 5/2013 | Cropper et al. | |
| 8,474,459 | B2 | 7/2013 | Schnell | |
| 8,517,932 | B2 | 8/2013 | Sakai, Jr. et al. | |
| 8,517,934 | B2 * | 8/2013 | Reznick | A61B 17/3421 600/206 |
| 8,771,223 | B2 * | 7/2014 | Patton | A61B 17/3421 604/93.01 |
| 8,795,235 | B2 * | 8/2014 | Mastri | A61B 17/3421 600/204 |
| 8,795,326 | B2 * | 8/2014 | Richard | A61B 17/3423 600/206 |
| 8,821,392 | B2 * | 9/2014 | Lozman | A61B 17/1684 600/204 |
| 8,905,937 | B2 * | 12/2014 | Ellingwood | A61B 5/053 600/481 |
| 9,211,234 | B2 * | 12/2015 | Tai | A61B 17/3415 |
| 9,314,269 | B2 * | 4/2016 | Webb | A61B 17/3462 |
| 2003/0158572 | A1 * | 8/2003 | McFarlane | A61B 17/3421 606/192 |
| 2005/0049624 | A1 * | 3/2005 | Francese | A61B 17/3421 606/185 |
| 2005/0119685 | A1 * | 6/2005 | Smith | A61B 17/3439 606/198 |
| 2007/0162066 | A1 * | 7/2007 | Lyon | A61B 17/3421 606/191 |
| 2008/0086165 | A1 * | 4/2008 | Lyon | A61M 25/0017 606/191 |
| 2008/0242930 | A1 * | 10/2008 | Hanypsiak | A61B 17/3421 600/114 |
| 2009/0105659 | A1 * | 4/2009 | Bettuchi | A61B 17/3421 604/180 |
| 2009/0124862 | A1 * | 5/2009 | Cohen | A61B 1/00154 600/235 |
| 2009/0149716 | A1 * | 6/2009 | Diao | A61B 1/00085 600/202 |
| 2009/0204081 | A1 * | 8/2009 | Whittaker | A61B 17/3421 604/264 |
| 2010/0240959 | A1 * | 9/2010 | Donahue | A61B 17/3421 600/204 |
| 2011/0034775 | A1 * | 2/2011 | Lozman | A61B 17/1684 600/204 |
| 2011/0144437 | A1 * | 6/2011 | Ortiz | A61B 17/3421 600/201 |
| 2011/0144440 | A1 * | 6/2011 | Cropper | A61B 17/3421 600/203 |
| 2011/0144447 | A1 * | 6/2011 | Schleitweiler | A61B 17/3421 600/210 |
| 2011/0144590 | A1 * | 6/2011 | Sakai, Jr. | A61B 17/3421 604/167.01 |
| 2011/0251464 | A1 * | 10/2011 | Kleyman | A61B 17/3423 600/206 |
| 2012/0157781 | A1 * | 6/2012 | Kleyman | A61B 17/3423 600/208 |
| 2012/0323081 | A1 | 12/2012 | Son | |
| 2013/0150654 | A1 * | 6/2013 | Stanfield | A61M 1/10 600/16 |
| 2014/0031630 | A1 * | 1/2014 | Nguyen | A61B 17/0218 600/204 |
| 2014/0276945 | A1 * | 9/2014 | Pravong | A61M 39/02 606/130 |
| 2014/0296647 | A1 * | 10/2014 | Kucklick | A61B 17/3423 600/204 |
| 2014/0364697 | A1 * | 12/2014 | Son | A61B 1/32 600/215 |
| 2016/0038018 | A1 * | 2/2016 | Wilson | A61B 17/3421 600/114 |
| 2016/0038133 | A1 * | 2/2016 | Smith | A61B 17/320016 600/204 |
| 2016/0045220 | A1 * | 2/2016 | Wachli | A61B 17/3423 600/204 |
| 2016/0220271 | A1 * | 8/2016 | Mastri | A61B 17/0218 |

(56) References Cited

U.S. PATENT DOCUMENTS

2016/0296221 A1* 10/2016 Morris .................. A61F 9/0008
2016/0331401 A1* 11/2016 Dreyfuss ............ A61B 17/3423

* cited by examiner

SURGICAL CANNULA SYSTEM AND METHOD OF USE

FIELD

The present disclosure relates generally to methods, systems, and devices for providing access to a patient's body during a surgical procedure.

BACKGROUND

A variety of surgical procedures require providing surgical access to an internal body cavity and/or joint of a patient through portals created by the insertion of a rigid cannula and obturator into an intended pathway through the patient's tissue. This access allows surgeons to pass instruments through the portals and to operate on the internal body cavity or joint of the patient using these instruments. As an example, in arthroscopic surgical procedures, a surgeon may pass a variety of elongated instruments through a cannula to access an internal body cavity, such as a knee or shoulder joint, to perform an operation. Flexible cannulas may offer some advantages in terms of tissue holding ability but can be more difficult to insert. Currently, a common insertion method for placing a cannula into an intended pathway through tissue of a patient involves positioning the cannula perpendicularly to the intended pathway and then folding the cannula into the pathway, commonly by using a curved clamp.

This approach to insertion can be cumbersome. For example, the method may cause trauma and/or damage to the tissue around the portal as the cannula is folded and turned into the pathway. This tearing of the surrounding tissue can enlarge the portal.

Accordingly, there remains a need for improved methods, systems, and devices for use in surgery requiring the use of flexible cannulas.

SUMMARY

In one embodiment, a cannula effective as a surgical portal is provided. The cannula includes an elongate flexible body having a cylindrical shaft with a longitudinal axis extending therethrough. The shaft also has a proximal end and a distal end. A flexible and elastic annular dam is formed on the distal end of the shaft. The dam has an unconstrained diameter greater than a diameter of the shaft. A hub is formed on the proximal end of the shaft. The hub has a diameter greater than the diameter of the shaft. A lumen extends through the body along the longitudinal axis of the shaft. The lumen has a first opening at a proximal end of the hub. The lumen also has a second opening at the distal end of the shaft. A flexible, expandable sleeve is removably disposed on the distal end of the shaft. The flexible sleeve covers the dam. The flexible sleeve is also configured to place the dam in a constrained condition in which a constrained diameter of the dam is approximately equal to a diameter of the shaft at a distal end thereof.

In some embodiments, the dam can comprise a plurality of separated petals. The plurality of petals can overlap each other. The plurality of petals can be in the range of two to five petals. The cannula can also have a flexible nut movably disposed on the shaft between the hub and the dam. The cannula shaft can be threaded. A natural-state diameter of the sleeve can be less than the diameter of the shaft of the elongate flexible body.

In another embodiment, a surgical system is provided. The surgical system includes a flexible cannula having an elongate, generally cylindrical body. The body includes an elongate shaft extending between a proximal hub and a distal dam. A lumen extends through the cannula along a longitudinal axis thereof. The dam is in the form of a flexible annular member formed on a distal end of the shaft. The dam has an unconstrained diameter greater than a diameter of the shaft. The hub also has a diameter greater than the diameter of the shaft. The system further includes an obturator. The obturator has an elongate shaft. The shaft is configured to be removably positioned within the lumen of the cannula. The shaft is also configured to fit within the lumen in a clearance fit. The system further includes a flexible, expandable sleeve. The sleeve is removably positioned on the distal end of the shaft of the cannula. The sleeve deformably encapsulates the dam such that the dam is folded against the shaft of the cannula.

In various embodiments, the sleeve and the dam are elastic. The surgical system can further include a spacer. The spacer can be removably positioned on the shaft of the obturator between the proximal hub of the cannula and a proximal end of a handle of the obturator. The spacer can be configured to prevent relative movement between the obturator and the cannula. The spacer can also be in the form of a substantially rigid sleeve. The obturator can be configured such that a distal end of the obturator shaft protrudes from the distal end of the cannula shaft and a portion of the sleeve can be removably attached to the distal end of the obturator shaft. A diameter of the lumen extending through the cannula can also be sized and configured to allow simultaneous passage therethrough of the obturator shaft and the attached sleeve. The surgical system can also include a length of the obturator shaft that is greater than a length of the lumen extending through the cannula. The cannula shaft can also have surface features formed thereon. The surface features can be threads. The dam can include a plurality of separated petals. A natural-state diameter of the sleeve can also be less than the diameter of the cannula shaft.

In another embodiment, a method of providing access to a surgical site is provided. The method includes inserting a cannula system through an incision in a patient. The cannula system includes an obturator having an elongate distal shaft. The system also includes a soft, flexible cannula removably disposed on the shaft of the obturator. The cannula has a cannula shaft extending between a proximal hub and a distal dam. The cannula also has a lumen extending through the cannula shaft from the proximal hub to an opening at a distal end of the cannula shaft. The cannula further includes an elastic sleeve. The sleeve is removably positioned over the distal end of the cannula shaft so as to cover the dam and constrain the dam against a portion of the cannula shaft. The method further includes positioning the distal end of the cannula shaft and the dam within a joint space. The method also includes advancing the obturator shaft relative to the cannula. The elastic sleeve is removed from the dam and remains attached to a distal end of the obturator shaft. The dam is thus enabled to expand to an unconstrained diameter. The method also includes withdrawing the obturator and sleeve from the cannula. Withdraw is accomplished by passing the obturator shaft and the sleeve through the lumen of the cannula shaft in the proximal direction. The method includes allowing the cannula to remain in position to enable one or more surgical tools to be passed through the lumen.

In various embodiments, the method can include that, prior to positioning, the cannula system further has a spacer removably positioned on the cannula shaft proximal to the hub. The spacer can maintain a relative position between a handle of the obturator and the hub. The method can further include removing the spacer before advancing the obturator shaft relative to the cannula.

BRIEF DESCRIPTION OF DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The apparatus, systems, and methods described herein can provide a surgeon the ability to insert a cannula into an intended pathway through tissue of a patient while minimizing the potential for damage to any tissue of the patient surrounding the pathway during insertion and still allowing the cannula to be structurally sound. A flexible cannula is provided with a shaft extending between a dam on its distal end and a hub on its proximal end. Both the dam and the hub have diameters that are typically greater than a diameter of the shaft. The shaft may have surface features formed thereon, such as a thread. The shaft may also have a nut placed thereon, which can be advanced along the threads or other features of the shaft. For example, the nut may be rotatably placed on the thread and can be movable along the shaft. The dam, like the cannula, is flexible and can be formed of separable or separated petals. A removable sleeve removably covers the dam so that the dam can achieve a constrained configuration with a reduced diameter, thus minimizing the risk of tissue damage during cannula placement. The sleeve is used to compress the dam prior to or during insertion of the cannula into an intended pathway of the patient such that the diameter of the dam is approximately equal to that of the shaft of the cannula. Upon removal of the sleeve, following placement of the cannula, the dam may expand to its unconstrained diameter, securing the cannula in the intended pathway through the tissue of the patient. This cannula system provides a secure, structurally-sound portal into an internal body cavity or joint of the patient while minimizing the potential for damage to the tissue of the patient.

Figure 1:
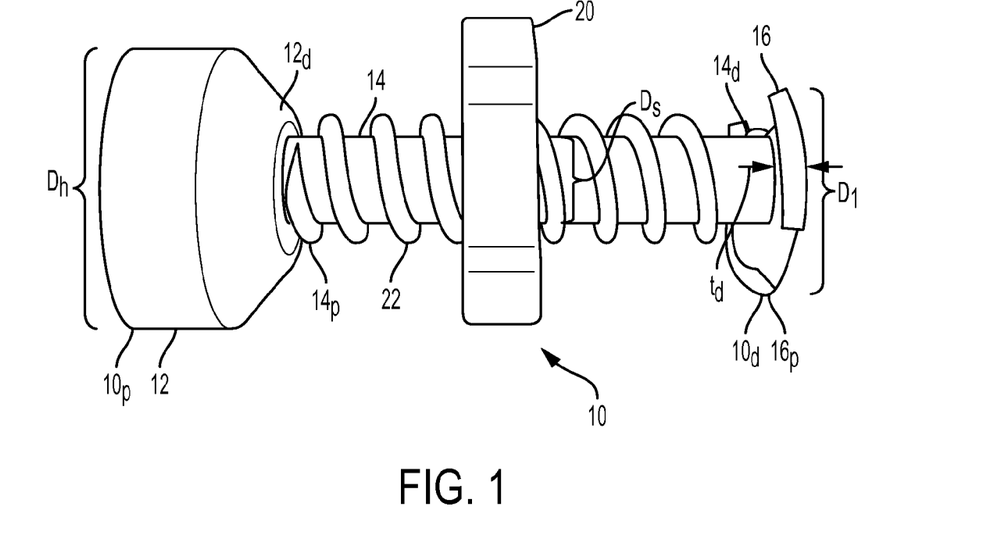
FIG. 1 is a side view of an embodiment of a cannula.
Figure 2:
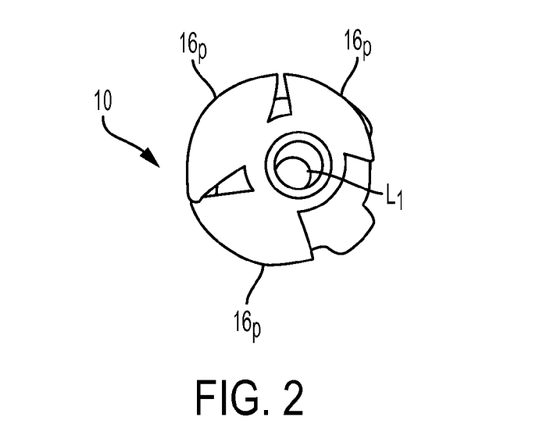
FIG. 2 is an end view of the cannula of FIG. 1.
Figure 3:
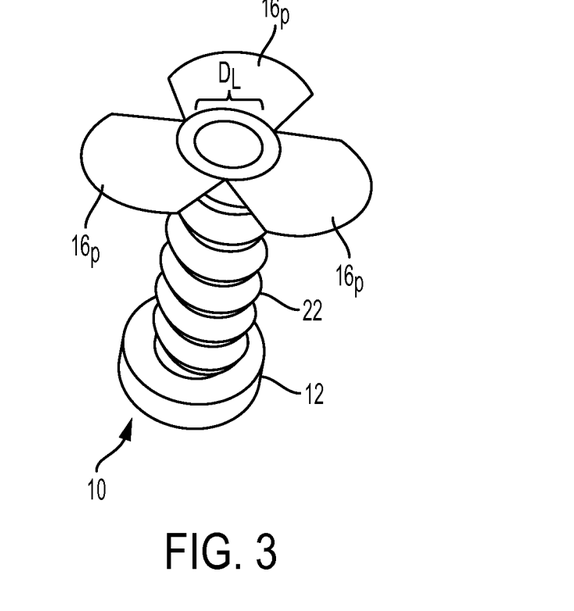
FIG. 3 is a representation of the cannula of FIG. 1 without a nut.
Figure 4:
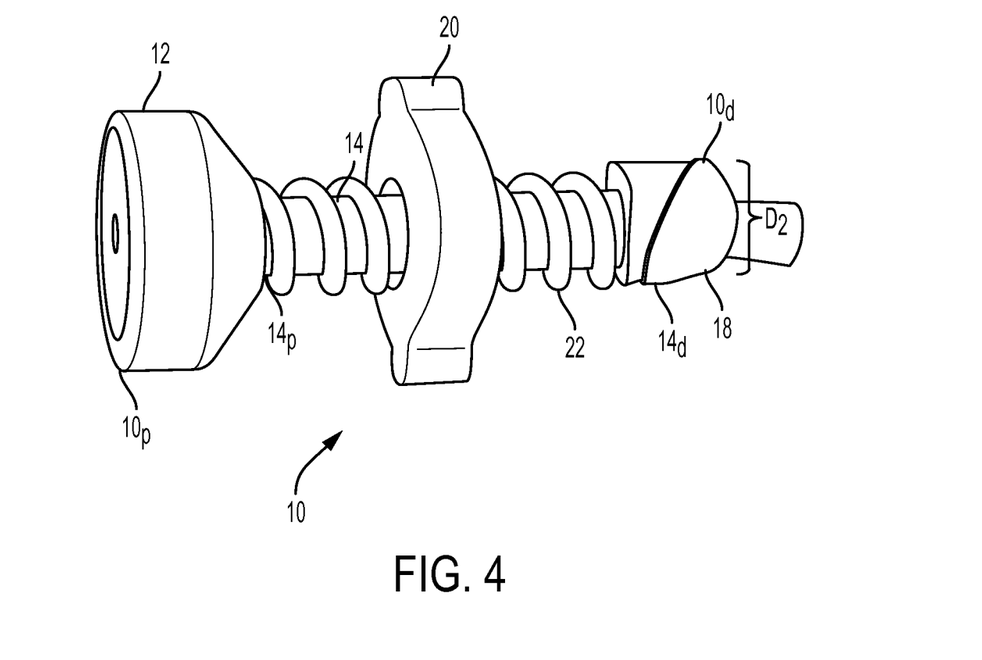
FIG. 4 is a side view of the cannula of FIG. 1 with an elastic sleeve.

FIGS. 1-4 illustrate an example of a cannula useful with the cannula system described herein. As shown in FIG. 1, cannula 10 is in the form of a generally elongate flexible body having a proximal end $10_p$ and a distal end $10_d$ with a lumen $L_1$ (shown in FIG. 2) extending therethrough. The proximal end $10_p$ of the cannula 10 includes a hub 12. An elongate shaft 14 extends distally from the hub 12 and a flexible dam 16 extends from the shaft at a distal end $10_d$ of the cannula. FIG. 1 shows the structure of the cannula 10 with the dam 16 in an unconstrained configuration while FIG. 4 shows the dam 16 in a constrained configuration with a removable sleeve 18 applied thereto such that the dam 16 is compressed against an outer wall of the shaft 14.

The hub 12 forms the proximal end $10_p$ of the cannula 10. The hub 12 is symmetrically cylindrical and has a tapered distal end 12d where the hub 12 connects to the shaft 14. A proximal end of the hub 12 has an opening for the lumen $L_1$. The hub 12 has a diameter $D_h$ greater than a diameter $D_s$ of the shaft 14. While the diameter $D_h$ of the hub 12 can be equal to or greater than a diameter $D_1$ of the unconstrained dam 16, it can be any diameter that is operable with the cannula, including a diameter that is greater than the diameter $D_1$ of the unconstrained dam 16. As an example, the diameter $D_h$ of the hub 12 can be in the range of about 15 mm to 25 mm at the proximal end.

As described above, the shaft 14 extends distally from the hub 12 and terminates with the dam 16. The diameter $D_s$ of the shaft 14 is less than the diameter $D_h$ of the hub 12 and the diameter $D_1$ of the unconstrained dam 16. The diameter $D_s$ can be any diameter that is still operable with the cannula 10. As an example, the diameter $D_s$ of the shaft 14 can be in the range of about 5 mm to 15 mm. A length $L_s$ of the shaft 14 can be any length that is operable with the cannula 10, such as in the range of about 30 mm to 120 mm. The shaft 14 can have one or more surface features formed thereon and the surface features can optionally accommodate a movable nut 20. In one embodiment, shown in FIG. 1, the shaft 14 has a surface feature in the form of a helical thread 22 formed thereon. The thread 22 extends approximately from the hub 12 to the annular dam 16. However, the thread 22 may cover any portion of the shaft 14 or may not be provided on the shaft 14 at all. Additionally, the thread 22 may terminate before the distal end $14_d$ of the shaft 14 to allow the dam 16 to be more easily compressed against the shaft 14.

The nut 20 is disposed on the thread 22 and is rotatable along the thread 22 such that the nut 20 moves between the hub 12 and the annular dam 16. The nut 20 is movable along the shaft 14 to secure the cannula 10 in place through a tissue of a patient. For example, once the cannula 10 is placed within the tissue of the patient, the nut 20 is rotatable to cause the nut 20 to move distally along the shaft 14. The nut 20 is rotatable until it contacts an external side of the tissue of the patient. The distal movement of the nut 20 thus allows any thickness of the tissue of the patient to be secured between the dam 16 and the nut 20 of the cannula 10 without having to alter the length of the shaft 14.

The annular dam 16 is formed on the distal end of the shaft 14. In the unconstrained configuration the dam 16 has a diameter $D_1$ greater than the diameter $D_s$ of the shaft 14. The dam 16 has a constrained diameter $D_2$ approximately equal to the diameter $D_s$ of the shaft 16, as shown in FIG. 4. A person skilled in the art will appreciate that the constrained diameter $D_2$ of the dam 16 is approximately equal to the diameter $D_s$ of the shaft 14 but for a thickness $t_d$ of the dam and the size of any threads or other surface features formed on the shaft. The diameter $D_1$ can be any diameter that is operable with the cannula 10. As an example, the diameter $D_1$ can be in the range of about 10 mm to 25 mm. The dam 16 has petals $16_p$. As shown in the illustrative embodiment in FIG. 2, the petals $16_p$ are three separated petals that overlap each other when the petals $16_p$ are folded back against the shaft 14. However, one skilled in the art will appreciate that any number of petals can be used, for example in the range of two to five, as well as a symmetrically or asymmetrically cylindrical shape for the dam 16. The petals can have any width that is still operable with the cannula 10. For example, the petals $16_p$ in FIG. 2 have a width in the range of about 10 mm to 20 mm. The thickness of the petals $16_p$ can also vary as long as the petals $16_p$ are able to be compressed against the shaft 14 but still provide anchoring support for the cannula when it is implanted within a patient. By way of example, the thickness of the petals $16_p$ can be in the range of about 1 mm to 3 mm. As explained below, the annular dam 16 is made of sufficiently resilient material such that removal of a compressing force from the petals $16_p$ of the distal dam 16 will cause the petals $16_p$ of the distal dam 16 to expand to the unconstrained diameter $D_1$.

The cannula 10 and its various components can be made of an elastic, flexible material. Suitable materials from which the cannula and its components can be formed include those that are biocompatible and have properties that provide sufficient flexibility to enable ease of insertion into a patient's body while still providing structural integrity once implanted. Exemplary suitable properties include a Shore A durometer in the range of about 20-60. Exemplary materials include a variety of biocompatible polymers. Examples of suitable polymers include medical-grade silicone, polychloroprene, styrene-butadiene, polyisoprene, and latex rubber. The components on the cannula 10 may be all made of the same material or any or all components may be made of different materials, depending on the desired material and structural properties of the cannula 10.

An elastic sleeve is removably placed over the annular dam to compress the dam. In the illustrative embodiment in FIG. 4, the elastic sleeve 18 is placed over the distal end $14_d$ of the shaft 14 so as to cover the annular dam 16 and constrain the petals $16_p$ of the annular dam 16 against the shaft 14. The natural-state inner diameter of the elastic sleeve 18 is less than the diameter $D_s$ of the shaft 14, enabling it to provide a constraining force against the annular dam 16 when the elastic sleeve 18 is removably in place. The elastic sleeve 18 can extend distally beyond the distal end $14_d$ of the shaft 14. As with the cannula 10, the elastic sleeve 18 can be made of a flexible, elastic material, such as any number of polymer biocompatible materials, as will be appreciated by one skilled in the art. Exemplary materials include medical-grade silicone, polychloroprene, styrene-butadiene, polyisoprene, and latex rubber. Exemplary suitable properties include Shore A durometer in the range of about 20-60. The elastic sleeve can be any length and diameter capable of compressing the dam 16. For example, the elastic sleeve can have a length in the range of about 15 mm to 40 mm and an inner diameter in the range of about 5 mm to 10 mm. The elastic sleeve 18 may be placed over the annular dam 16 and the distal end $14_d$ of the shaft 14 through a variety of approaches, such as with a clamp, as would be understood by a person skilled in the art.

The lumen $L_1$, which extends through the cannula 10 along its length, has a diameter in the range of about 4 mm to 14 mm.

The cannula described above may interact with any number of systems, devices, and methods that allow a surgeon the ability to insert the cannula into an intended pathway through tissue of a patient. For example, a surgical system is provided that may incorporate the cannula and an obturator.

Figure 5:
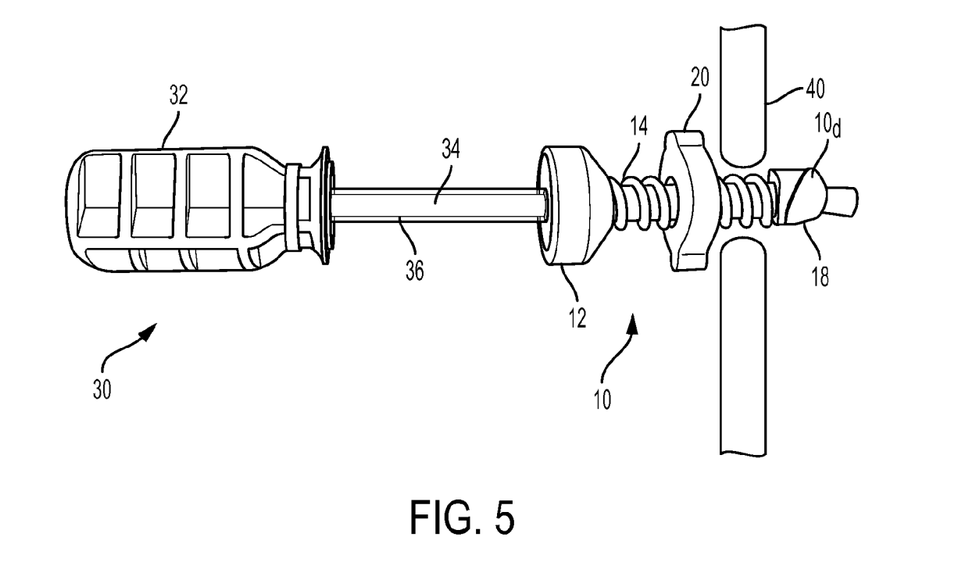
FIG. 5 is a side view of an embodiment of an obturator and spacer with the cannula of FIG. 1.
Figure 6:
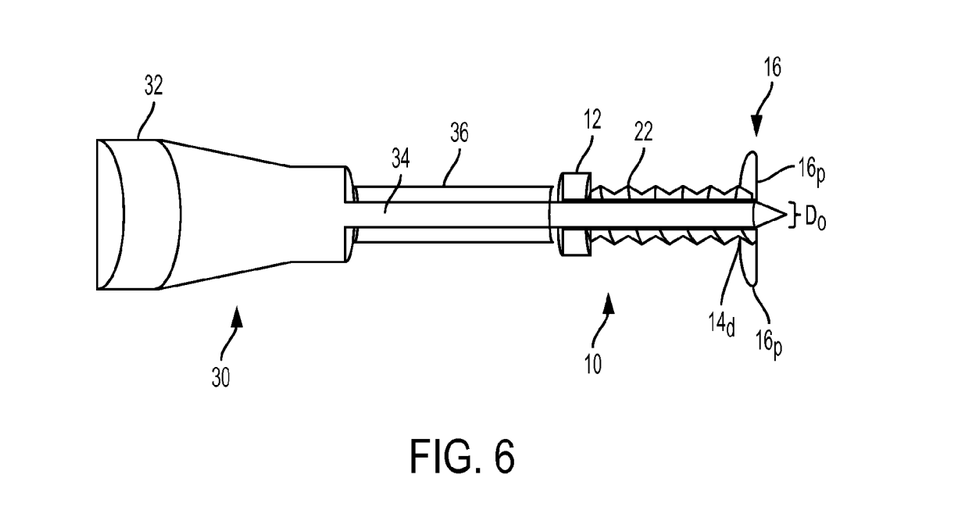
FIG. 6 is a representation of the obturator and the cannula of FIG. 5 without the nut.
Figure 7:
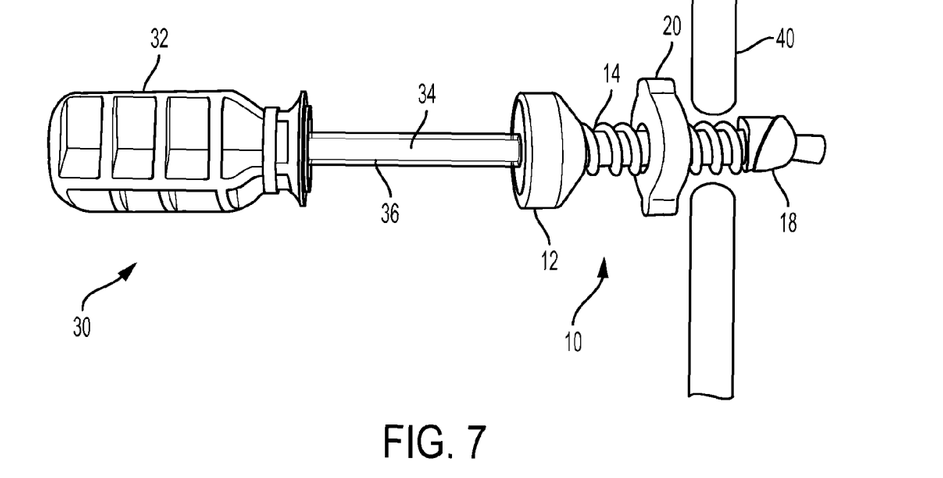
FIG. 7 is a side view illustrating the obturator and the cannula of FIG. 5 disposed through tissue of a patient.

FIGS. 5-11 illustrate a system that includes a cannula of the type described above and an obturator 30. As shown, the obturator 30 has a handle 32 placed at a proximal end of the obturator 30 with a shaft 34 extending distally from the handle 32, wherein the shaft is sized and configured to be inserted through the lumen $L_1$ of the cannula 10 of FIG. 2. The shaft 34 is a generally elongate, cylindrical member which can have a tapered or pointed distal end as shown in FIG. 6. When configured as a system with cannula 10, the shaft 34 extends through the lumen $L_1$ of the cannula 10, as shown in FIGS. 5-7, such that the distal end of the shaft 34 extends beyond the distal end $14_d$ of the shaft 14 of the cannula 10. A person skilled in the art will appreciate that the length of the obturator shaft 34 can be any length that enables it to extend through lumen $L_1$ of cannula 10 and extend beyond the distal end $10_d$ of the cannula 10. In one example, the obturator shaft is sized such that the distal end of the obturator 30 extends beyond the cannula 10 by a distance sufficient to ensure that the sleeve 18 is removed from the annular dam 16 and compressed along its full length on the obturator shaft 34 as the obturator shaft is extended beyond the distal end of the cannula. For example, the length of the obturator shaft 34 can be in the range of about 50 mm to 150 mm. Similarly, the diameter $D_O$ of the obturator shaft 34 should be such that the shaft 34 can pass through the lumen L1 with or without the sleeve 18 attached to the distal end of the shaft 34. As an example, the diameter $D_O$ can be in the range of about 2 mm to 12 mm. As the distal end of the obturator shaft 34 can be enclosed by the elastic sleeve 18, one skilled in the art will understand that the diameter $D_O$ of the obturator shaft 34 is greater than the natural-state inner diameter of the elastic sleeve 18, resulting in the elastic sleeve 18 removably attaching to the distal end of the shaft 34 of the obturator 30. Further, the natural-state diameter of the elastic sleeve 18 can be small enough to secure tightly to the distal end of the shaft 34 such that the elastic sleeve 18 tightly encloses at least part of the distal point of the shaft 34. Thus the obturator shaft 34 with the elastic sleeve 18 attached to a distal end thereon can pass through the lumen $L_1$. The obturator 30 can be formed of any medical-grade material, such as any number of plastics and/or metals, as will be appreciated by one skilled in the art (for example a rigid polymer, such as polycarbonate or ABS).

A spacer 36 is removably placed on the shaft 34 of the obturator 30 between the handle 32 of the obturator 30 and the hub 12 of the cannula 10. The spacer 36 maintains the relative positions between the cannula 10 and the obturator 30. The spacer 36 of FIG. 5 comprises a substantially rigid sleeve of a material, such as a polymer. The spacer 36 may have a longitudinal slit (not shown) to facilitate removal of the spacer 36. However, as will be appreciated by one skilled in the art, the spacer 36 may take any form and be composed of any material such that the spacer 36 maintains the relative positions between the cannula 10 and the obturator 30. For example, the spacer 36 can comprise a peg insertable into a hole (not shown) on the shaft 34 or a movable tab and slot (not shown) formed on the shaft 34 and be made of any number of polymers or other materials.

Figure 8:
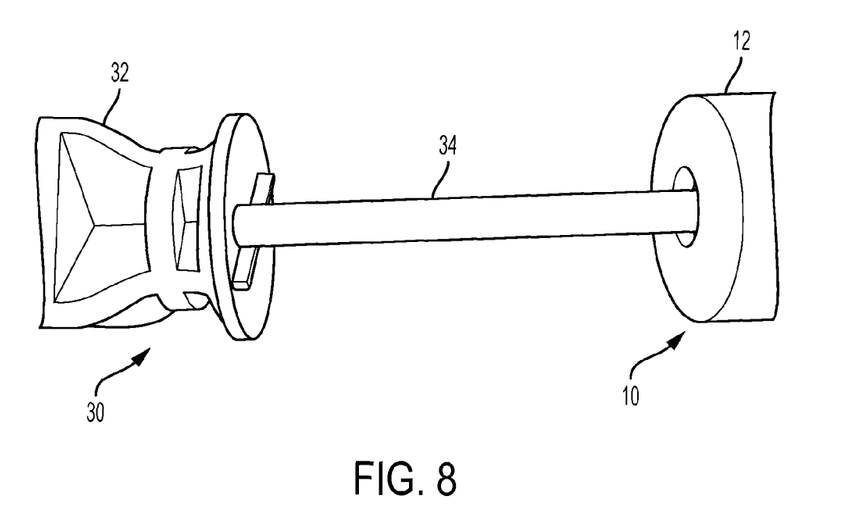
FIG. 8 is a side view of part of the obturator and the cannula of FIG. 8 without the spacer.
Figure 9:
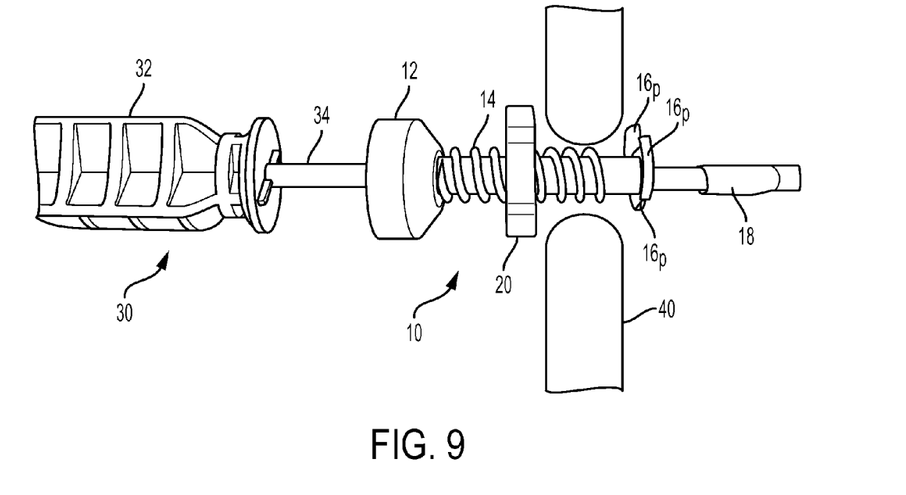
FIG. 9 is a side view of the obturator and the cannula of FIG. 7 with the sleeve removed from the cannula.

In use, the obturator 30 is inserted through the cannula 10, and the elastic sleeve 18 is placed over the distal ends of the cannula 10, as shown in FIG. 5, causing the petals $16_p$ to compress against the shaft of the cannula 10. FIG. 5 also illustrates the spacer 36 removably placed on the shaft 34 of the obturator 30. As so configured, the system can be inserted through an incision in a patient, such that the distal end $10_d$ of the cannula 10 and the dam 16 are positioned within a body cavity or joint capsule through a desired pathway of tissue 40 of the patient, as shown in FIG. 7. At this point, the spacer 36 is removed, as shown in FIG. 8, allowing relative movement between the obturator 30 and the cannula 10. The obturator 30 is then advanced distally relative to the cannula 10, causing the shaft 34 to extend further into the body cavity or joint capsule of the patient beyond the distal end $10_d$ and the dam 16 of the cannula, as shown in FIG. 9. As the obturator shaft 34 is further advanced relative to the cannula 10, the elastic sleeve 18 attached to the distal end of the obturator shaft 34 moves distally with the distal motion of the shaft 34. This distal movement of the shaft 34 and the elastic sleeve 18 causes the elastic sleeve 18 to pull free of the dam 16 while remaining attached to the shaft 34. Once freed from the constraint of the sleeve 18, the dam 16 expands to its unconstrained diameter $D_1$, allowing the petals $16_p$ to expand so as to be perpendicularly oriented with respect to a longitudinal axis of the shaft 14. Once the dam 16 expands within the body cavity or joint capsule of the patient, the nut 20 can be moved distally to about tissue 40 to secure the cannula 10 within the patient.

Figure 10:
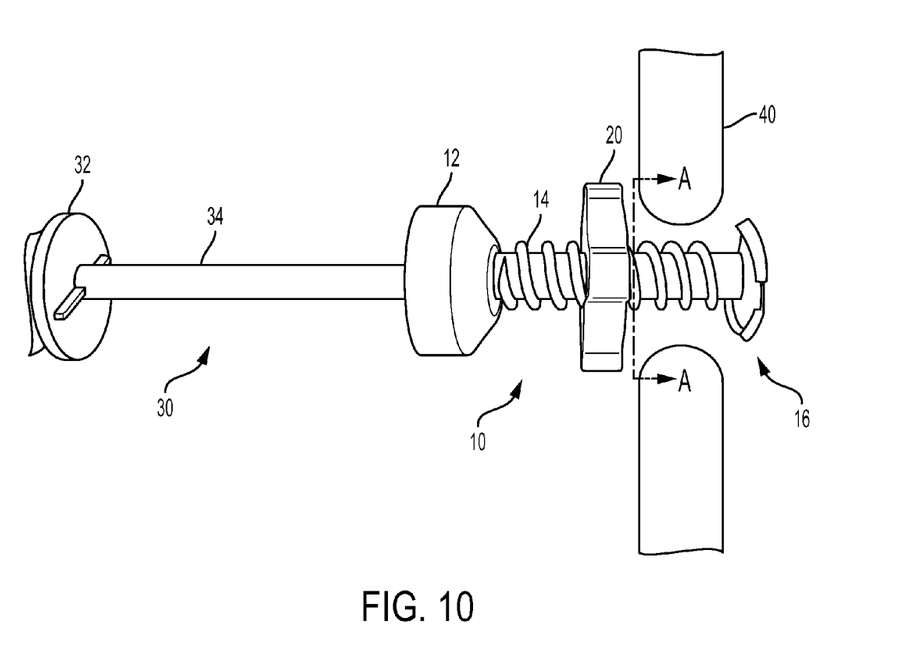
FIG. 10 is a side view of the obturator and the cannula of FIG. 7 as the obturator is being withdrawn.
Figure 11:
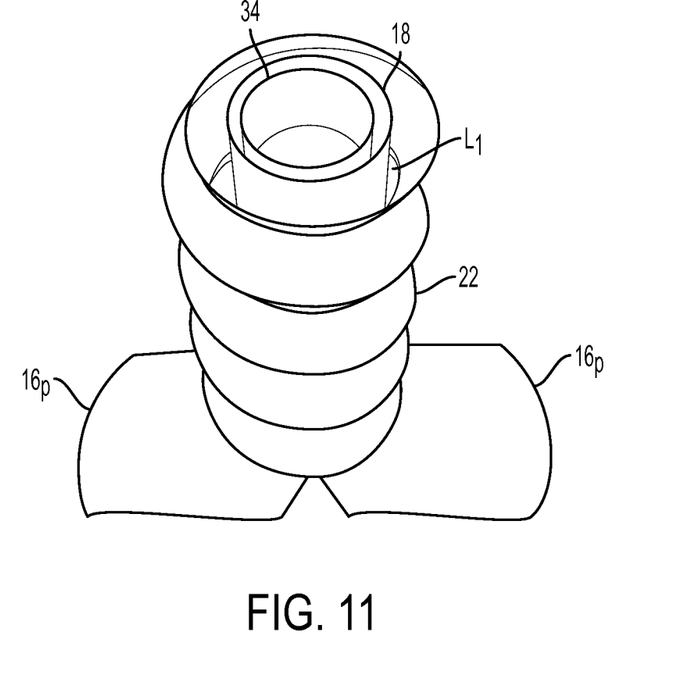
FIG. 11 is a representation of a perspective view taken across line A of FIG. 10.

As shown in FIG. 10, the elastic sleeve 18 and the distal end of the shaft 34 are withdrawn from the body cavity of the patient through the lumen $L_1$ after the cannula 10 is properly positioned and secured. The diameter $D_L$ of the lumen $L_1$ is greater than the diameter of the shaft 34 with the attached sleeve 18, as shown in FIG. 11, enabling the shaft 34 with the attached sleeve 18 to be withdrawn through the lumen $L_1$. The cannula 10 remains in the portal through the tissue 40, allowing a surgeon to pass instruments through the lumen $L_1$ and into the body cavity of the patient.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. One skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
    a flexible cannula having an elongate, generally cylindrical body with an elongate shaft extending between a proximal hub and a distal dam, and a lumen extending through the cannula along a longitudinal axis thereof, wherein the dam is in the form of a flexible annular member formed on a distal end of the shaft, the dam has an unconstrained diameter greater than a diameter of the shaft, and the hub has a diameter greater than the diameter of the shaft;
    an obturator having an elongate obturator shaft configured to be removably positioned within the lumen of the cannula, the obturator shaft being configured to fit within the lumen in a clearance fit; and
    a flexible, expandable sleeve removably positioned on the distal end of the shaft of the cannula, the sleeve deformably partially encapsulating the dam such that the dam is folded against the shaft of the cannula.

2. The surgical system of claim 1, wherein the flexible sleeve and the dam are elastic.

3. The surgical system of claim 1, further comprising a spacer removably positioned on the obturator shaft between the proximal hub of the cannula and a proximal end of a handle of the obturator, wherein the spacer is configured to prevent relative movement between the obturator and the cannula.

4. The surgical system of claim 3, wherein the spacer is in the form of a substantially rigid sleeve.

5. The surgical system of claim 1, wherein the obturator is configured such that a distal end of the obturator shaft protrudes from the distal end of the cannula shaft, and a portion of the sleeve is removably attached to the distal end of the obturator shaft.

6. The surgical system of claim 1, wherein a diameter of the lumen extending through the cannula is sized and configured to allow simultaneous passage therethrough of the obturator shaft and the attached flexible sleeve.

7. The surgical system of claim 1, wherein a length of the obturator shaft is greater than a length of the lumen extending through the cannula.

8. The surgical system of claim 1, wherein the cannula shaft has surface features formed thereon.

9. The surgical system of claim 8, wherein the surface features are threads.

10. The cannula of claim 1, wherein the dam comprises a plurality of separated petals.

11. The cannula of claim 1, wherein a natural-state diameter of the sleeve is less than the diameter of the cannula shaft.

12. A surgical system, comprising:
a flexible cannula having an elongate, generally cylindrical body with an elongate shaft extending between a proximal hub and a distal dam, and a lumen extending through the cannula along a longitudinal axis thereof, wherein the dam is in the form of a flexible annular member formed on a distal end of the shaft, the dam has an unconstrained diameter greater than a diameter of the shaft, and the hub has a diameter greater than the diameter of the shaft;
an obturator having an elongate obturator shaft configured to be removably positioned within the lumen of the cannula, the obturator shaft being configured to fit within the lumen in a clearance fit; and
a flexible, expandable sleeve removably positioned on the distal end of the shaft of the cannula, the sleeve deformably encapsulating the dam such that the dam is folded against the shaft of the cannula, the sleeve being configured to be removed by the obturator.

13. The surgical system of claim 12, wherein the flexible sleeve and the dam are elastic.

14. The surgical system of claim 12, further comprising a spacer removably positioned on the obturator shaft between the proximal hub of the cannula and a proximal end of a handle of the obturator, wherein the spacer is configured to prevent relative movement between the obturator and the cannula.

15. The surgical system of claim 14, wherein the spacer is in the form of a substantially rigid sleeve.

16. The surgical system of claim 12, wherein the obturator is configured such that a distal end of the obturator shaft protrudes from the distal end of the cannula shaft, and a portion of the sleeve is removably attached to the distal end of the obturator shaft.

17. The surgical system of claim 12, wherein a diameter of the lumen extending through the cannula is sized and configured to allow simultaneous passage therethrough of the obturator shaft and the attached flexible sleeve.

18. The surgical system of claim 12, wherein a length of the obturator shaft is greater than a length of the lumen extending through the cannula.

19. The cannula of claim 12, wherein the dam comprises a plurality of separated petals.

20. The cannula of claim 12, wherein a natural-state diameter of the sleeve is less than the diameter of the cannula shaft.

* * * * *